United States Patent [19]
Albanese

[11] Patent Number: 5,551,086
[45] Date of Patent: Sep. 3, 1996

[54] HAND RESTRAINT DEVICE

[76] Inventor: Michael Q. Albanese, 1552 Leatherleaf Dr., Las Vegas, Nev. 89123

[21] Appl. No.: 498,088

[22] Filed: Jul. 3, 1995

[51] Int. Cl.$^6$ .............................. A61F 5/37; A41D 13/08
[52] U.S. Cl. ....................... 2/158; 2/16; 70/16; 128/879
[58] Field of Search .............................. 2/158, 159, 160, 2/162, 16, 17, 20, 161.6; 128/879, 878; 70/16, 18, 15, 17

[56] References Cited

U.S. PATENT DOCUMENTS

| | | | |
|---|---|---|---|
| 404,544 | 6/1889 | James et al. | 70/16 |
| 973,330 | 10/1910 | Wood | 2/158 |
| 1,010,199 | 11/1911 | Stedman | 2/162 |
| 1,397,624 | 11/1921 | Epling | 128/879 |
| 1,456,580 | 5/1923 | Sullivan | 2/162 |
| 2,043,153 | 6/1936 | Cox . | |
| 2,084,183 | 6/1937 | Blendinger . | |
| 3,176,683 | 4/1965 | Posey . | |
| 3,182,657 | 5/1965 | Zurbuchen . | |
| 3,253,589 | 5/1966 | Shook | 2/16 |
| 3,417,840 | 12/1968 | Farnsworth, Jr. | 2/160 |
| 3,476,108 | 11/1969 | Matukas | 2/16 |
| 3,741,207 | 6/1973 | Fuson | 2/16 |
| 4,471,495 | 9/1984 | Kruse et al. | 2/162 |
| 4,698,850 | 10/1987 | Patton, Sr. et al. | 2/159 |
| 4,741,051 | 5/1988 | Bible | 2/158 |
| 4,887,616 | 12/1989 | Baijnath | 128/879 |
| 5,031,641 | 7/1991 | Upton | 70/16 |
| 5,050,596 | 9/1991 | Walasek et al. | 2/158 |
| 5,230,351 | 7/1993 | Nyorkor | 70/16 |
| 5,343,562 | 9/1994 | Bible | 2/158 |
| 5,349,966 | 9/1994 | Garcia | 2/158 |
| 5,369,257 | 11/1994 | Gibbon | 2/158 |
| 5,375,263 | 12/1994 | Cuccia | 2/17 |
| 5,379,179 | 1/1995 | Graves | 2/16 |

*Primary Examiner*—Amy B. Vanatta
*Attorney, Agent, or Firm*—Quirk & Tratos

[57] ABSTRACT

A hand restraint device for restraining the hands of an individual and preventing them from using their fingers and thumbs is disclosed. The hand restraint device comprises a pair of mitts for connection to a pair of standard handcuffs. The mitts comprise pockets of material with a closed end and open end for enveloping the hands of the wearer. Each mitt includes a durable hand enclosure and elastic wristband. The handcuffs encircle the wearer's wrists, passing through a ring connected to the outside of the wristband of each mitt. A rib is located at the open end of each mitt on the outside of each wristband, preventing the wearer from sliding the mitts from underneath the handcuffs.

6 Claims, 2 Drawing Sheets

HAND RESTRAINT DEVICE

FIELD OF THE INVENTION

The present invention relates to a device for restraining the hands of an individual such as a criminal. More particularly, the invention is a device for use with standard handcuff bracelets which prevents the individual from using his fingers and thumbs.

BACKGROUND OF THE INVENTION

A recurring problem for law enforcement officials is how to adequately restrain a prisoner during arrest and transport. Normally, law enforcement officials attempt to restrain the criminal by handcuffing his hands together.

As is well known, handcuffs comprise a pair of linked circular bands or bracelets which are selectively lockable about the criminal's wrists. Typically, a chain connects the bands or cuffs.

Handcuffs are effective in preventing a criminal from separating his hands by a distance greater than the length of the chain between the cuffs. The handcuffs thus limit the range of movement of the hands and arms of the criminal. Because a criminal's hands are linked together, the movement of the criminal's arms with respect to his body is also limited. For this reason, handcuffing a criminal's hands behind his back is especially effective.

While handcuffs are effective in limiting a criminal's movement of his hands with respect to one another and of his arms with respect to his body, the handcuffs do not restrain his fingers and thumbs. Thus, occasionally, a handcuffed criminal has grasped a nearby gun or similar item and escaped law enforcement or caused injury.

Others have proposed devices for restraining the hands of individuals. These devices have not been easy to use, are not convenient, or are too complex.

SUMMARY OF THE INVENTION

The present invention is a device for restraining the hands of an individual. In particular, the device comprises a pair of mitts for location over the hands of an individual to prevent the wearer from using his fingers and thumbs. Advantageously, the device of the present invention is useful with standard handcuffs. The mitts of the present invention are useful with a pair of standard handcuffs to handcuff an individual's hands together, and prevent the individual from using his fingers and thumbs.

The mitts comprise sleeves of material having an outer surface, and a closed end and an open end forming an interior pocket. The mitts have a hand-enveloping portion of a durable Cordura™ material and an elastic wristband at the open end. Preferably, extensions of the durable hand-enveloping portion extend across the wristband along the sides of each mitt.

A ring is connected to the extension of each mitt at the wristband section. Each ring is preferably a rectangular link of plastic connected with a loop of material to the mitt. Each ring has an inner dimension sized to allow passage of a handcuff therethrough.

A rib of material encircles the wristband at the open end of each mitt. Preferably, the rib comprises a Cordura™ cord of circular cross-section attached to the wristband.

In use, the mitts are placed over a wearer's hands. A handcuff passes through each ring on each mitt, encircling the wearer's wrists over the outside of the wristband. The handcuffs are closed and locked around the wearer's wrist.

The mitts prevent the wearer from using his fingers or thumbs. Advantageously, the handcuffs prevent the wearer from removing the mitts, and handcuff the wearer's hands together.

The elastic wristband material hugs the wearer's wrists, preventing the wearer from slipping items into the mitts, and making it more difficult for the wearer to pull the mitts off. The rib on each mitt prevents the user from sliding the handcuff over and off the wristband of the mitt in an attempt to remove the mitt from his hand.

Further objects, features, and advantages of the present invention over the prior art will become apparent from the detailed description of the drawings which follows, when considered with the attached figures.

DETAILED DESCRIPTION OF THE PREFERRED EMBODIMENT

Figure 1:
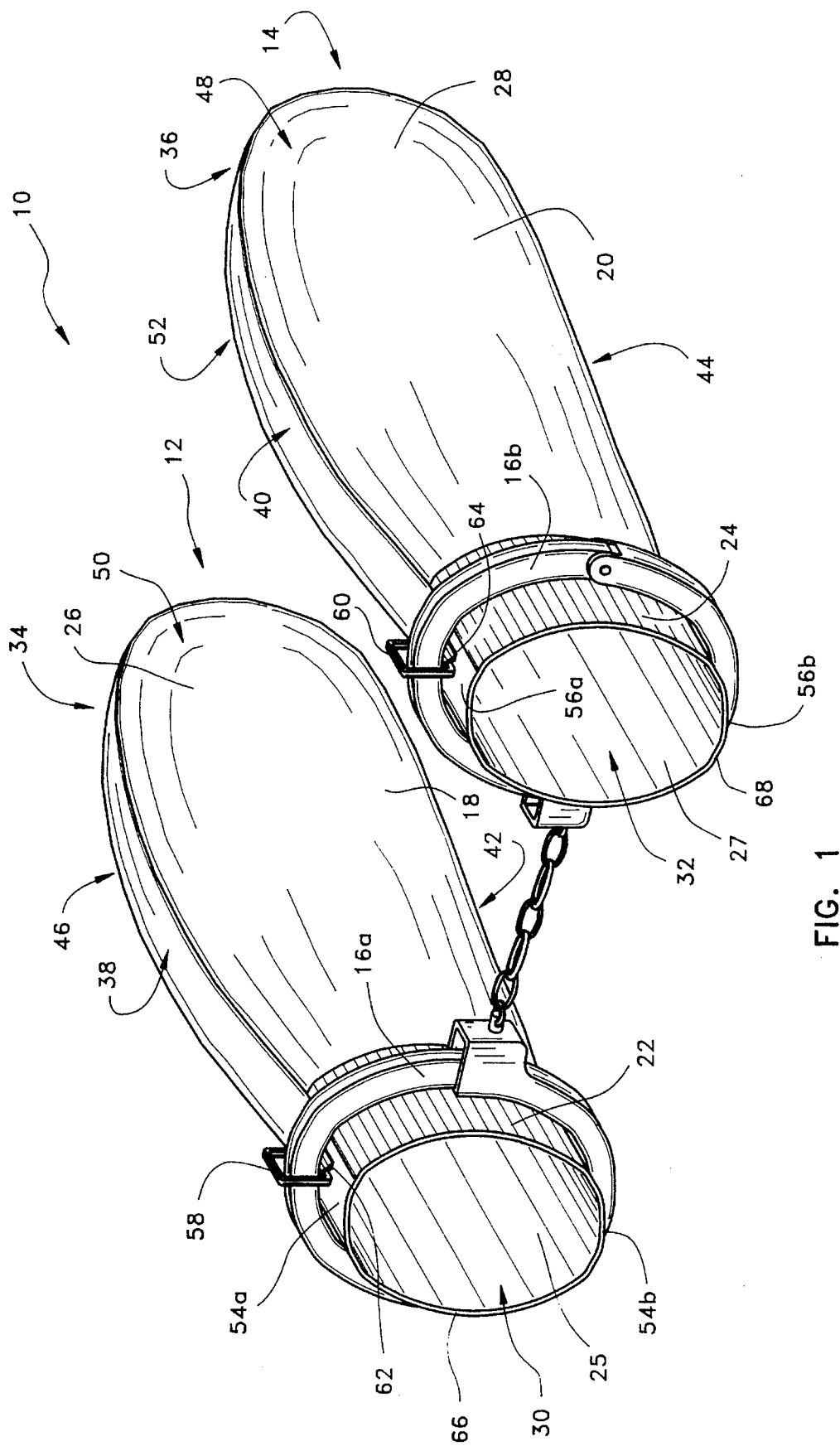
FIG. 1 is a perspective view of the hand-restraining device of the present invention illustrating two mitts connected by a pair of handcuffs.
Figure 2:
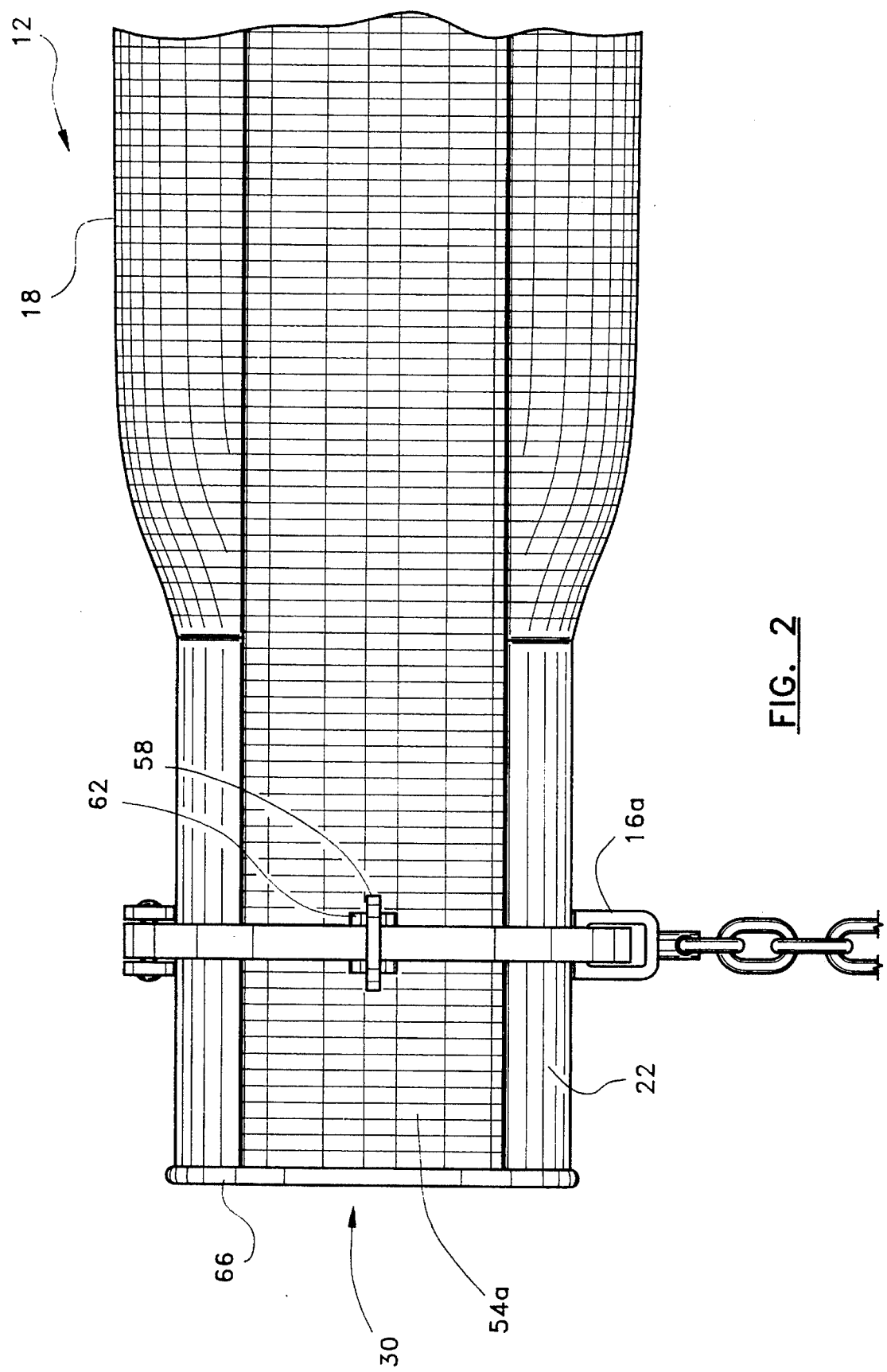
FIG. 2 is a top view of one of the mitts illustrated in FIG. 1.

FIGS. 1 and 2 illustrate a device 10 for restraining the hands of an individual in accordance with the present invention. In general, the device 10 comprises a first mitt 12 and a second mitt 14 for connection with a pair of handcuffs 16a,b.

Each mitt 12,14 comprises an enclosed sleeve of material sized to envelop a person's hand and a portion of their wrist. Each mitt 12,14 preferably comprises a hand enclosure 18,20, and a wristband 22,24. A rigid plastic ring 58,60 is mounted on an outer surface 26,28 of each mitt 12,14 with a loop 62,64 of material for engagement with the handcuffs 16.

In use, the mitts 12,14 are placed over the wearer's hands in the position shown in FIG. 1. Each handcuff 16a,b is passed through the ring 58,60 and around the outside of the wristband 22,24 of the mitt 12,14 which covers the wrist of the wearer. Each handcuff 16a,b is locked, preventing the wearer from removing the mitts 12,14, and precluding the wearer's use of his fingers and/or thumbs to grasp objects and the like.

Referring again to FIGS. 1 and 2, the device 10 of the present invention will be described in detail. Each mitt 12,14 comprises a sleeve such that the mitt has an inner surface 25,27, an outer surface 26,28, an open end 30,32, and closed end 34,36.

The hand enclosure 18,20 of each mitt 12,14 comprises a pocket of material for enveloping a wearer's hand. To comfortably accommodate the wearer's hands, the mitts 12,14 are preferably elliptical in shape, having a width from a top side 38,40 (corresponding to the "thumb" side of the wearer's hands) to a bottom side 42,44 which is greater than the thickness from a front or outwardly facing surface 46,48 (corresponding to the "top" of a wearer's hands), to a back or inwardly facing surface 50,52 (corresponding to the "palm" of a wearer's hand). For example, the width of the mitts 12,14 may be about 5 to 6 inches, and the thickness may be about 1.5 to 2 inches.

Preferably, two reinforcing extensions 54a,b and 56a,b for supporting the rings 58,60 extend from the hand enclosure 18,20 along the sides of each mitt 12,14 across the wristband 22,24. Each extension 54a,b 56a,b thus coterminates with the wristband 22,24 at the open end 30,32 of the mitt 12,14.

Preferably, the hand enclosure 18,20 and extensions 54a,b 56a,b of each mitt 12,14 are constructed from a durable, fairly slick and semi-rigid fabric or similar material, such as the nylon based fabric material called Cordura™ available from DuPont. This material is preferred because it is fairly rigid and slick, making it difficult for a wearer to grab items through the mitt 12,14. Also, material such as Cordura™ is very durable, reducing the possibility that the wearer will tear or wear a hole in the material of the mitt 12,14, allowing him to use his fingers and thumb. While Cordura™ is the preferred fabric, other materials having similar properties and satisfying the criteria stated above may be useful.

The wristband 22,24 is positioned at the open end 30,32 of each mitt 12,14, extending from the hand enclosure 18,20 of each mitt. Thus, the wristbands 22,24 serve to lengthen the hand enclosure of each mitt 12,14.

Preferably, the wristbands 22,24 comprise an elastic cloth material. This material "clings" to the wearer's wrist, helping keep the mitts 12,14 in place, and reducing the possibility that the wearer can slip something into the mitts 12,14.

A rib, lip or bead 66,68 encircles the wristband 22,24 of each mitt 12,14 at the open end 30,32 thereof. This lip 66,68 preferably comprises a cord of semi-rigid durable material such as Cordura™, and preferably has a circular cross-section. As illustrated in FIG. 2, the lip 66,68 is connected to the wristband 22,24 on the outer surface 26,28 of the mitt 12,14, thus extending outwardly therefrom.

The rings 58,60 are attached to the exterior of the top side 38,40 of each mitt 12,14. Each ring 58,60 preferably comprises a rectangular loop or link of plastic having an interior dimension greater than the outer dimension of the handcuff 16a,b used therewith. When rectangular in shape, the rings 58,60 preferably extend lengthwise outwardly from the mitts 12,14 for engagement with the handcuffs 16a,b.

The rings 58,60 are preferably connected to each mitt 12,14 by a small loop 62,64 of material attached to the wing 54a, 56a located on the top side 38,40 of each mitt.

Use of the restraining device 10 of the present invention is as follows. First, the mitts 12,14 are pulled onto and over an individual's hands. The mitts 12,14 are oriented in such a manner than the side of each mitt having the ring 58,60 thereon corresponds to the "thumb" side of the wearer's hand. The double bar or lock portion of each handcuff 16a,b is placed on the side of the mitt 12,14 opposite the ring, and the free end of the handcuff is passed through the ring 12,14 and secured in the double-bar lock. At this time, each handcuff 16a,b, passes around the wearer's wrist in such a manner to secure the mitts 12,14 over the wearer's hands, but do not cause discomfort or injury.

Advantageously, the device 10 of the present invention reduces the possibility that the wearer can use his fingers and/or thumbs. The mitts 12,14 are useful with a pair of standard handcuffs, thus further restricting the wearer's use of his hands. Moreover, when used with handcuffs, the wearer can not remove the mitts. In particular, the handcuffs 16a,b tightly engage the wearer's wrists, and at the same time pass through the rings 58,60 on the mitts 12,14, preventing the wearer from removing the mitts without removing the handcuffs. The connection of the mitts 12,14 to the handcuffs 16a,b to accomplish these features is also simple and quick.

As stated above, the wristband 22,24 of each mitt 12,14 is preferably constructed of an elastic material so that it hugs the wearer's wrist. The engagement of the elastic wristbands 22,24 with the wearer's wrists also serves to make it difficult for the wearer to remove the mitts 12,14. however.

The wristband 22,24 may be made of other materials. For example, the wristband 22,24 may just be a narrower extension of the hand enclosing portion 18,20. In any case, the wristband 22,24 is preferably a portion of the mitt 12,14 which extends slightly beyond the wearer's hand and over a portion of the wrist, to protect the wearer's wrist from the handcuff. In that instance, it may be desirable to provide a cinch strap, or hook and loop fastener or similar means for constricting the wristband material tightly around the wearer's wrists.

The rib, bead or lip 66,68 on each mitt 12,14 serves to make it more difficult for a wearer to slip the handcuffs 16a,b over and off the wristband portion of each mitt. In particular, when the handcuffs 16a,b are secured around the wearer's wrists, the outwardly extending semi-rigid lips 66,68 act as a barrier to removal of the handcuffs.

The rings 58,60 which connect the handcuffs 16a,b and mitts 12,14 may have any of several shapes, and be constructed of any durable, relatively non-breakable material. For example, the rings 58,60 may comprise steel loops. Preferably, however, and as stated above, the rings 58,60 have an inner dimension close to the outer dimension of the handcuffs to reduce the possibility of the wearer breaking the rings by through movement of the cuffs within the rings.

The loops 62,64 of material which connect the rings 58,60 to the mitts 12,14 may themselves comprise steel, plastic or similar rings which are connected to the mitts 12,14 by sewing, rivets, or similar means. The loops 62,64 are preferably connected to the wings 54a, 56a when the wings 54a, 56a are made of Cordura™ (or similar material) because this material is generally more durable than the elastic material of the wristbands 22,24.

The extensions 54a,b 56a,b are preferably Cordura™ material not only to strengthen the portion of the mitt 12,14 where the rings 58,60 are connected, but to increase the useful life of the mitts. In particular, rubbing of the handcuffs 16a,b against the soft elastic cloth wristband 22,24 may wear the wristbands excessively. The extensions 54a,b 56a,b serve to reduce the wear of the mitts 12,14 at the points where the cuffs most frequently contact the mitts: the areas comprising the intersection of the top and bottom sides 38–42 with the front and back 46–52 of the outer surface 26,28 of the mitts 12,14.

It will be understood that the above described arrangements of apparatus and the method therefrom are merely illustrative of applications of the principles of this invention and many other embodiments and modifications may be made without departing from the spirit and scope of the invention as defined in the claims.

I claim:

1. A hand restraint device for use with a pair of handcuffs for preventing a wearer from using his fingers or thumbs comprising:
   a pair of mitts, each mitt having a hand-enveloping section having a first closed end, a second end, an outer surface, and an interior pocket for enveloping the hand of a wearer, said hand-enveloping section constructed of a durable, semi-rigid material, and each mitt further including a wrist-engaging section extending from said second end of said hand-enveloping section, said wrist-engaging section comprising at least one strip of said material forming said hand-enveloping section and the remainder thereof constructed of an elastic material, said elastic material and said strip forming a wrist-encircling band at said second end of said hand-enveloping section;

a ring connected to an outer surface of said strip of durable, semi-rigid material included in said wrist-engaging portion of each of said mitts for engagement by said handcuffs; and a rib located on each of said wrist-encircling bands at an end thereof opposite said closed end of said hand-enveloping portion of said mitts.

2. The hand restraint device of claim 1, wherein said rings comprise rectangular members connected to said mitts with a loop of material.

3. A method of restraining the hands of an individual with a pair of handcuffs comprising first and second wrist-encircling bands connected by a flexible member and a hand restraint device for use with a pair of handcuffs comprising a pair of mitts, each mitt having an outer surface, an interior pocket, and an open end and a closed end, said mitts having a first hand enveloping portion and a second wristband portion and a ring located on said outer surface of each of said mitts, comprising:

locating one of said mitts over each hand of the individual to be restrained;

passing one of said bands of said pair of handcuffs through the ring located on one of said mitts and locking said band about said wristband portion of said mitt; and passing the other of said bands of said pair of handcuffs through the ring located on the other mitt and locking said band about said wristband portion of that mitt.

4. In combination, a pair of handcuffs and a pair of mitts, said pair of handcuffs comprising first and second wrist-encircling bands connected by a flexible member, and said mitts each comprising a flexible sleeve having an enclosed end comprising an inner pocket, accessible through an open end, and a rigid ring fastened to an outer surface of each of said mitts, said first wrist-encircling band extending through one of said rings and said second wrist-encircling band extending through the other of said rings.

5. The combination of claim 4, wherein said mitts include a hand enveloping portion and wristband.

6. The combination of claim 4, wherein a rib is located on said mitt at said open end.

* * * * *